US006827698B1

(12) United States Patent
Kleinekofort

(10) Patent No.: US 6,827,698 B1
(45) Date of Patent: Dec. 7, 2004

(54) METHOD AND DEVICE FOR DETERMINING BLOOD FLOW IN A VASCULAR ACCESS

(75) Inventor: Wolfgang Kleinekofort, Kelkheim (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/549,364

(22) Filed: Apr. 14, 2000

(30) Foreign Application Priority Data

Apr. 16, 1999 (DE) .......................... 199 17 197

(51) Int. Cl.[7] .................. A61M 37/00; A61M 31/00; A61M 1/36; C02F 1/44
(52) U.S. Cl. .................. 604/6.06; 604/4.01; 604/5.01; 604/5.04; 604/67; 210/645; 422/44
(58) Field of Search ................ 604/4.01, 5.01, 604/5.04, 19, 28, 65–67, 6.06; 210/645–647, 85, 90, 97, 100, 101, 515, 739, 782; 422/44

(56) References Cited

U.S. PATENT DOCUMENTS

| | | | | |
|---|---|---|---|---|
| 3,946,731 A | * | 3/1976 | Lichtenstein | 128/DIG. 3 |
| 5,454,374 A | * | 10/1995 | Omachi | 600/486 |
| 5,830,365 A | * | 11/1998 | Schneditz | 210/646 |
| 6,167,765 B1 | * | 1/2001 | Weitzel | 600/454 |
| 6,346,084 B1 | * | 2/2002 | Schnell et al. | 600/485 |

FOREIGN PATENT DOCUMENTS

| | | |
|---|---|---|
| DE | 40 24 434 | 2/1992 |
| DE | 195 41 783 | 3/1997 |

OTHER PUBLICATIONS

Depner, Thomas A., Techniques for prospective detection of venous stenosis, Adv. Ren. Repl. Ther. 1:119–130, 1994.*
Besarab, A and Frinak, S. The prevention of access failure pressure monitoring. ASAIO, 44:35–37, 1998.*

* cited by examiner

Primary Examiner—Angela D. Sykes
Assistant Examiner—Leslie R. Deak
(74) Attorney, Agent, or Firm—Kenyon & Kenyon

(57) ABSTRACT

A method and a device for determining the blood flow $Q_F$ in a vascular access (F) during an extracorporeal blood treatment is described, where the blood enters the blood treatment unit (3) of the blood treatment machine through an arterial branch (19) of an extracorporeal circulation loop (2) which is in fluid connection with the vascular access at an arterial connection. The blood is returned through a venous branch (21) of the extracorporeal circulation, which is in fluid connection with the vascular access at a venous connection (13). The blood flow in the vascular access is determined by measuring the pressure $P_{art}$, $P_{ven}$, in the arterial and/or venous branch of the extracorporeal circulation when the vascular access is open and interrupted, while the extracorporeal blood flow $Q_B$ is varied. Then the fistula flow $Q_F$ is determined from the measured values for the arterial and/or venous pressure while the vascular access is open and interrupted.

10 Claims, 3 Drawing Sheets

METHOD AND DEVICE FOR DETERMINING BLOOD FLOW IN A VASCULAR ACCESS

The present invention relates to a method of operating a blood treatment device for determining the blood flow in a vascular access during an extracorporeal blood treatment, and to a device for determining the blood flow in a vascular access during an extracorporeal blood treatment.

DESCRIPTION OF RELATED ART

In the methods used for chronic blood purification therapy such as hemodialysis, hemofiltration and hemodiafiltration, blood is sent through an extracorporeal circulation loop in a blood treatment unit, such as a dialyzer or filter. To serve as the access to the blood vessel system, an arteriovenous fistula is often created surgically and is then generally punctured with an arterial needle and venous needle (double needle dialysis). Likewise, use of a vascular implant (PTE graft) is also possible. The term "vascular access", as it is used below, is understood to refer to any type of access to a patient's blood vessel, but in particular to the connection between a patient's artery and vein.

Typical flows within a satisfactorily functioning vascular access are in the range of 1100 mL/min. Measurement of blood flow and vascular pressure is of crucial importance to monitoring the functioning of the access. Vascular implants showing a flow rate of less than 600 to 800 mL/min or an abnormal pressure are associated with a much higher risk of thrombosis. A thrombosis develops as a result of an unknown stenosis which leads to a reduction in blood flow in the vascular access. Through early detection of vascular accesses with a reduced blood flow, it is therefore possible to prevent imminent thromboses. In addition, by identifying vascular accesses with pathologically elevated flow rates above 2000 mL/min, overloading of the patient's cardiovascular system is prevented.

German Patent application 4 024 434 A1 describes a device for ultrafiltration monitoring in blood purification processes, having a pressure measurement device arranged in the extracorporeal blood circulation and an analyzer unit where the measured pressure values are stored in chronological order, and where a change in blood viscosity is deduced from a change in pressure values.

A device for measuring the flow through a fistula is described in German Patent 19 541 783 C1. This measurement of fistula flow is based on measuring the temperature in the arterial branch of the extracorporeal circulation while there occur variations in extracorporeal blood flow.

Another method of determining the blood flow in a vascular access is based on a measurement of recirculation before and after exchanging the arterial and venous blood tubes on the needles. This method yields good clinical results, but has the disadvantage that when the tubes are improperly exchanged, there is a risk of blood loss and infections, plus a residual pulmonary embolism risk.

In everyday clinical practice, the static pressure in the vascular access is measured after turning off the blood pump and the ultrafiltration unit. However, when the blood pump is stopped there is the risk of coagulation in the blood tubing system.

SUMMARY OF THE INVENTION

The present invention provides a method of operating a blood treatment device that makes it possible to determine the blood flow in the vascular system with high reliability, without any technical expense and without requiring that the blood tube connections be exchanged. This invention also provides a device that is relatively simple to implement technically, so that the blood flow in the vascular access can be determined with a high certainty without requiring that the blood tube connections be exchanged.

In one aspect, the invention is a method of operating a blood treatment machine for determining the blood flow $Q_B$ in a vascular access of an extracorporeal circulation during an extracorporeal blood treatment, the blood entering a blood treatment unit of the blood treatment machine through an arterial connection of an arterial branch in fluid connection with the vascular access, and is returned through a venous connection of a venous branch in fluid connection with the vascular access. The method comprises the steps of measuring pressures $P_{art}$, $P_{ven}$, $P_{art\ comp}$, $P_{ven\ comp}$ in one of the arterial or venous branch while the vascular access is open and blood flows through said vascular access between the arterial and venous connections, measuring the pressures while the vascular access is interrupted and no blood flows through the vascular access between the arterial and venous connections, varying blood flow $Q_B$ in the extracorporeal circulation, and determining the blood flow $Q_F$ in the open vascular access between the arterial and venous connections from the measured values of the pressures $P_{art}$, $P_{ven}$, $P_{art\ comp}$, $P_{ven\ comp}$.

In another aspect, the invention is a device for determining blood flow in a vascular access during an extracorporeal blood treatment, comprising an arterial branch of an extracorporeal circulation in fluid connection with the vascular access at an arterial connection, a blood treatment unit for receiving blood from the arterial branch, a venous branch of the extracorporeal circulation in fluid connection with the vascular access at a venous connection, and a blood pump connected to the extracorporeal circulation. The device also includes a control unit for varying the flow rate of the blood pump, at least one of an arterial and a venous measurement device for measuring pressures $P_{art}$, $P_{ven}$, $P_{art\ comp}$, $P_{ven\ comp}$ respectively in the arterial and venous branch of the extracorporeal circulation with the vascular access open and with the vascular access interrupted, means for varying a blood flow $Q_B$ in the extracorporeal circulation, a memory unit for storing the measured arterial and venous pressure, and a computer unit adapted to determine the blood flow $Q_B$ in the open vascular access from the measured values of the arterial and venous pressure $P_{art}$, $P_{ven}$, $P_{art\ comp}$, $P_{ven\ comp}$.

In the method according to this present invention, the blood flow in the vascular access is determined by performing a pressure measurement with an open vascular access while blood flows through the vascular access between the arterial and venous connections. The method also uses an interrupted vascular access while no blood flows through the same, while the blood flow in the extracorporeal circulation is varied. The blood flow in the open vascular access can then be determined from the measured values of the pressure in the vascular access that is open and interrupted. The blood flow can be determined either exclusively from the measured values for the pressure in the arterial branch, with the vascular access open and interrupted, or exclusively from the values for the pressure in the venous branch, with the vascular access open and interrupted.

However, it is also possible to use both the arterial pressure and the venous pressure values with both open and interrupted vascular access to determine the blood flow. The vascular access is preferably pressed by hand between the needles, which offers advantages in practice. This procedure can also be carried out with a compensation tube, a cuff or other similar device.

All measured values can be determined first with the vascular access open or interrupted, and only then are all the measured values determined with the vascular access in the other one of the interrupted or open condition, respectively, while the blood flow is varied within predetermined limits. The measured values can be recorded in two successive cycles, one with the vascular access open and one with it interrupted.

In a first variant of the claimed method, the blood flow can be determined in the extracorporeal circulation where the pressure in the arterial or venous branch, with the vascular access interrupted, is equal to the pressure in the arterial or venous branch, respectively, with the vascular access open. This step determines the blood flow in the open vascular access. In this case, the extracorporeal blood flow is equal to the blood flow in the vascular access. It is advantageous that only one pressure measurement, either in the arterial branch or in the venous branch, is necessary.

A second variant of this method provides for a measurement to be performed in the arterial and venous branches, to determine the blood flow in the extracorporeal circulation at which the pressure in the arterial branch having the vascular access interrupted is equal to the arterial pressure having the vascular access open. This method also determines the extracorporeal blood flow at which the venous pressure with the vascular access interrupted is equal to the venous pressure having the vascular access open. The blood flow in the open access is then advantageously determined by forming the average of these two extracorporeal blood flow values.

In another variant of this method, the difference between the pressure in the arterial branch having the vascular access interrupted and the pressure in the arterial branch having the vascular access open, and the difference between the venous pressure having the vascular access interrupted and the venous pressure having the vascular access open are determined as a function of the extracorporeal blood flow. For the case when the two differences are equal to zero, the extracorporeal blood flow is equal to the blood flow in the open vascular access.

The measured pressure values can be preferably stored in memory in chronological order. The parameters of a function representing the arterial and/or venous pressure as a function of the extracorporeal blood flow can be advantageously determined from the discrete measured values. Known mathematical procedures can be used to this end. Depending on the required accuracy, a larger or smaller number of measured values may be necessary. Outside of the defined limits, the arterial and/or venous pressure is advantageously determined by extrapolation of the function curve, so the blood flow need be varied only within relatively narrow limits.

The arterial and/or venous static pressure in the vascular access can also be determined from the measured values for the arterial and/or venous pressure in the extracorporeal circulation. To do so, by extrapolating the function curve, the arterial and/or venous extracorporeal pressure at which the extracorporeal blood flow is equal to zero is determined.

The invention described here includes an arterial and/or venous pressure measurement device for measuring the pressure in the respective arterial and/or venous branches. A control unit can be provided to permit variation of the extracorporeal blood flow by varying the flow rate of the blood pump installed in the extracorporeal circulation. The measured values can be stored in a memory unit. The blood flow in the vascular access can be calculated in a computer unit on the basis of the stored measured values.

BRIEF SUMMARY OF THE DRAWINGS

Various embodiments of the present invention are described in greater detail below with reference to the drawings.

In the Drawings.

DETAILED DESCRIPTION OF PREFERRED EMBODIMENTS OF THE INVENTION

Figure 1:
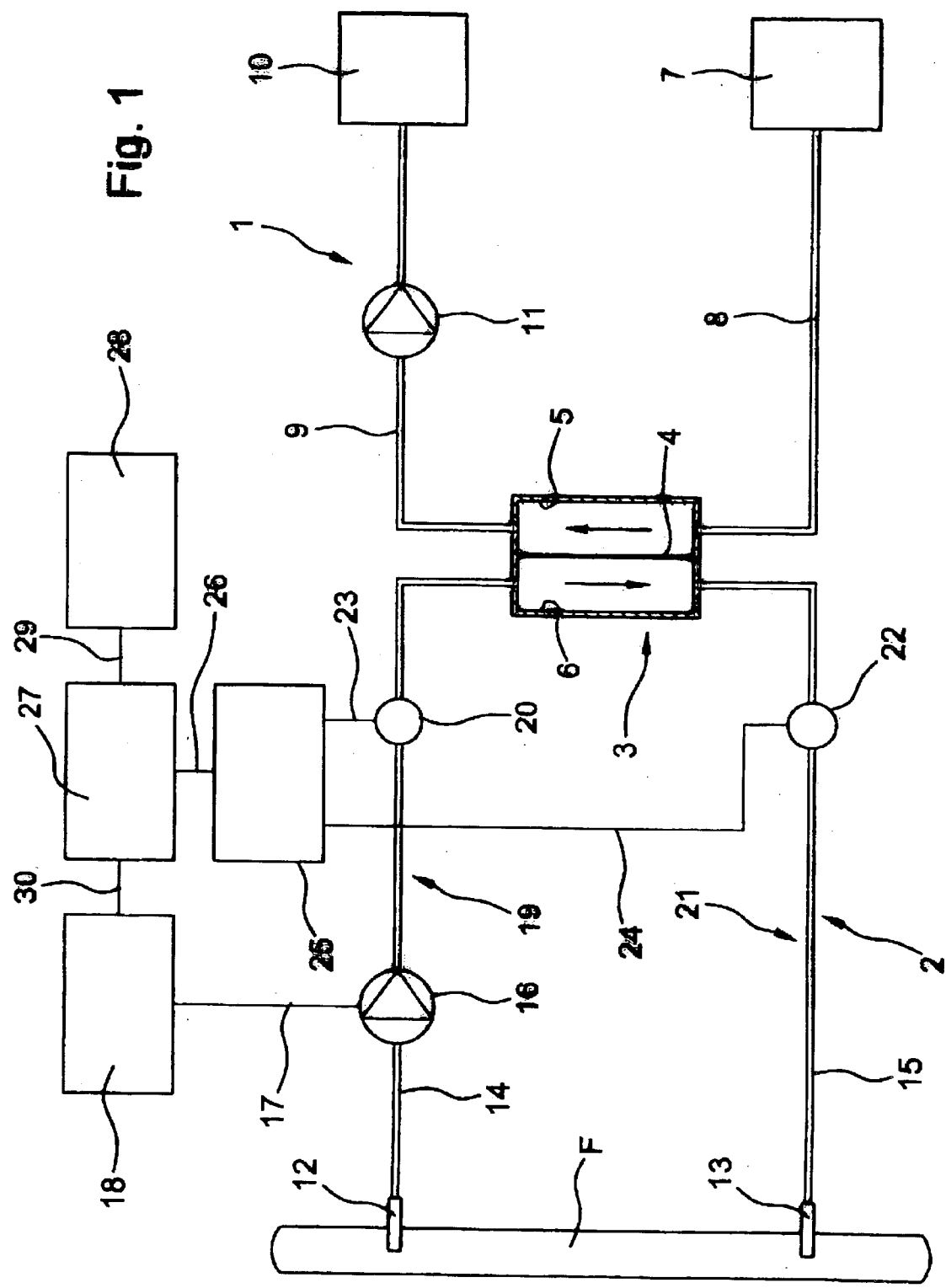
FIG. 1: shows a schematic diagram of a device according to the invention for determining the blood flow and the static pressure in the vascular access together with a dialysis.

The device according to the invention for determining the blood flow $Q_F$ in the vascular access (fistula flow) can be assembled, for example, as a separate component group. However, the device may also be part of the blood treatment machine, especially since some components used in the device are already present in known blood treatment machines. The device for determining the fistula flow, together with the necessary components of the blood treatment machine are described below. In one preferred embodiment, the blood treatment machine can be a conventional dialysis machine.

The dialysis machine can include a dialysis fluid circulation loop 1 and an extracorporeal blood circulation loop 2, between which there is a dialyzer 3 which is divided by a semipermeable membrane 4 into a dialysis fluid chamber 5 and a blood chamber 6. A dialysis fluid inlet line 8 leads from a dialysis fluid source 7 to the inlet of the dialysis fluid chamber, from whose outlet a dialysis fluid outlet line 9 leads to a drain 10. A dialysis fluid pump 11 can be connected to the dialysis fluid outlet line 9 to convey the dialysis fluid.

The patient's fistula F is punctured with arterial and venous needles 12, 13. A blood inlet line 14 leads from the arterial connection 12 to the entrance to the blood chamber 6, while a blood outlet line 15 leads from the outlet of blood chamber 6 to the venous connection 13. A blood pump 16 which determines the blood flow in the extracorporeal circulation can be connected to the blood inlet line 14 and also to a controlling unit 18 by a control line 17. The delivery of the blood pump 16 can be varied within a certain range with control unit 18.

An arterial pressure measurement device 20 can be provided to measure the pressure in the arterial branch 19, and a venous pressure measurement device 22 can be provided to measure the pressure in the venous branch 21 of the extracorporeal circulation. The two pressure measurement devices are connected by data lines 23, 24 to a memory unit 25 where the measured values are stored digitally in chronological order. This memory unit 25 can be connected by a data line 26 to a computer unit 27 which calculates the fistula flow and the static pressure in the fistula F from the measured values. The values thus determined can be displayed in a display unit 28 which is connected by a data line 29 to the computer unit 27. To control the program flow, the computer unit 27 in turn can be connected to the control unit 18 by a data line 30. The computer unit 27 may be, for example, a conventional microprocessor.

During an ongoing dialysis treatment, the arterial and venous pressures $P_{art}$ and $P_{ven}$ in the extracorporeal circulation loop 2 are determined as a function of the extracorporeal blood flow $Q_B$. Measurements yield the following functions:

$P_{art}$ ($Q_B$): arterial pressure in the extracorporeal circulation as a function of $Q_B$ $P_{ven}$ ($Q_B$): venous pressure in the extracorporeal circulation as a function of $Q_B$ After the measurement is concluded, pressure is applied to the vascular access between the arterial and venous needles, and the change in extracorporeal pressure is recorded as a function of the extracorporeal blood flow. Compression of a vascular access between the needles applied using either the fingers or a compression tube is an established clinical method of determining vascular resistance. In addition, it has been shown that the cardiac output does not change as a result of brief pressure on the vascular access, if the pressure lasts a time $t \leq 2$ min. To prevent artificial fluctuations in pressure, the patient should not move during the measurements. In addition, preferably there is no change in ultrafiltration rate. Thus, hemodynamic stability can be assumed during the measurement. These relations yield:

$P_{art\ comp}$ ($Q_B$): arterial pressure in the extracorporeal circulation loop 2 as a function of $Q_B$ after pressing on the vascular access.

$P_{ven\ comp}$ ($Q_B$): venous pressure in the extracorporeal circulation loop 2 as a function of $Q_B$ after pressing on the vascular access.

The pressures measured in the extracorporeal circulation loop 2, while the blood pump is operating, are composed of the dynamic pressure in the extracorporeal system and the dynamic pressure in the patient's vascular access. The dynamic pressure in the extracorporeal system is a function of the extracorporeal blood flow, the blood viscosity and the sum of the flow resistances in the extracorporeal circulation loop 2. The dynamic pressure in the patient's vascular access is a function of the systemic blood pressure and the systemic vascular flow resistances. The fistula pressure is thus a patient-specific parameter which also depends on the type of vascular access, the blood viscosity and the vascular system supplying blood to the vascular access. By analogy with the dynamic pressure in the extracorporeal system, a change in the fistula pressure, for example due to a fluctuation in blood pressure, to an increase in viscosity or to the patient changing positions, leads to a change in both the arterial and venous extracorporeal pressure reading.

Figure 2:
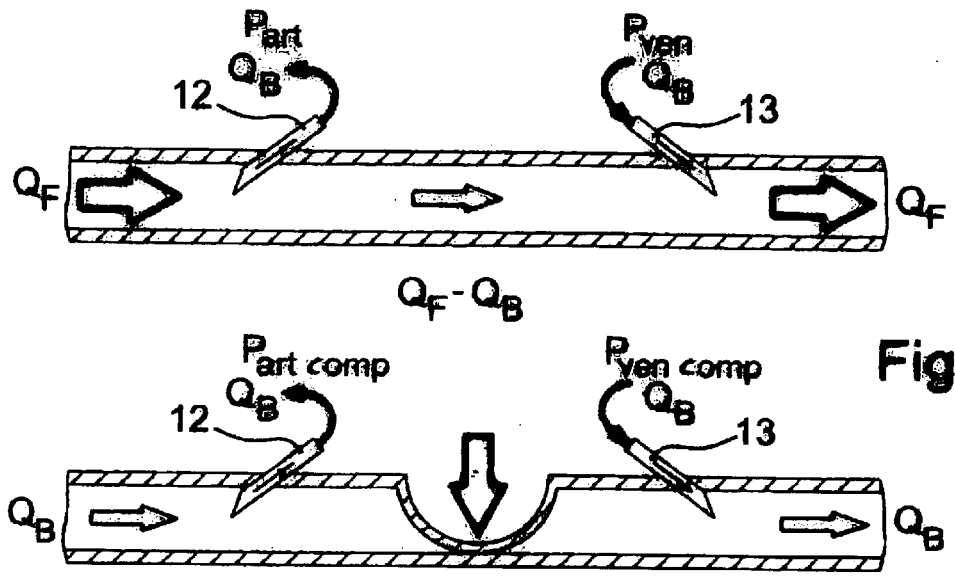
FIG. 2: schematically shows the change in pressure and/or flow when the vascular access is interrupted between the arterial and venous connections, when the blood flow in the vascular access is greater than the blood flow in the extracorporeal circulation.

FIG. 2 shows schematically the flow and pressure conditions before and after pressing on the fistula. The patient's systemic arterial blood pressure is available at the arterial needle 12 with the blood pump turned off and the vascular access pinched. The blood pressure may be, for example in the range of 50 to 150 mm Hg. The pressure at venous needle 13 corresponds to the venous return pressure in the patient's vascular access (3–15 mm Hg). With the vascular access open, the arterial pressure in the vascular access amounts to approximately 27 mm Hg with an intact fistula, and approximately 49 mm Hg with an intact PTFE graft. The venous pressure is approximately 17 mm Hg for the fistula or approximately 35 mm Hg for the graft.

With the blood pump running and the vascular access open, the fistula flow $Q_F$ is usually greater than the extracorporeal blood flow $Q_B$. In this case, a reduced fistula flow $Q_F$–$Q_B$ flows between the needles 12–13 in the vessel during the dialysis treatment. For the case when the extracorporeal blood flow is greater than the flow in the vessel ($Q_B$>$Q_F$), the difference $Q_F$–$Q_B$ is negative, i.e., there is a recirculation flow from the venous needle to the arterial needle. In the case when the extracorporeal blood flow is exactly equal to the flow in the vascular access, no blood flows through the vascular access between the arterial and venous needles. The three cases $Q_B$<$Q_F$, $Q_B$>$Q_F$ and $Q_B$=$Q_F$ are explained separately below.

$Q_B$<$Q_F$: In the case when the reduced flow $Q_F$–$Q_B$ between the arterial and venous needles is hindered, a dynamic pressure builds up at the arterial needle. Therefore, the arterial extracorporeal pressure $P_{art\ comp}$, increases. In this case, the higher the reduced flow $Q_F$–$Q_B$ is, the higher will be the dynamic pressure. On the other hand, the venous extracorporeal pressure $P_{ven\ comp}$ will drop, and as a result, the venous pressure drop will also depend on the reduced flow $Q_F$–$Q_B$.

$Q_B$=$Q_F$: In this limit case, there is no change in pressure and flow conditions when the vessel is pinched between the needles.

$Q_B$>$Q_F$: No recirculation occurs when the extracorporeal blood flow is greater than the flow in the vascular access. The recirculation flow from the venous to the arterial needle is stopped by compression of the vessel between the needles. This causes a drop in arterial extracorporeal pressure, where the resulting negative pressure difference depends on the recirculation flow. The venous extracorporeal pressure, however, increases slightly, because venous blood is prevented from flowing out by suppressing the recirculation flow.

The following table summarizes the arterial and venous pressure changes for the flow conditions described above.

| Delta $p_{art.}$ ($Q_B$) | Delta $p_{ven.}$ ($Q_B$) | Flow in the vascular access |
|---|---|---|
| + | − | $Q_B$ < $Q_F$ |
| 0 | 0 | $Q_B$ = $Q_F$ |
| − | + | $Q_B$ > $Q_F$ |

Where:

Delta $P_{art}(Q_B)$=$P_{art\ comp}(Q_B)$−$P_{art}(Q_B)$ (Equation 1)

Delta $P_{ven}(Q_B)$=$P_{ven\ comp}(Q_B)$−$P_{ven}(Q_B)$ (Equation 2)

A qualitative measurement of the flow in the vascular access is possible by performing a single pressure difference measurement, while the treatment is underway.

Figure 3:
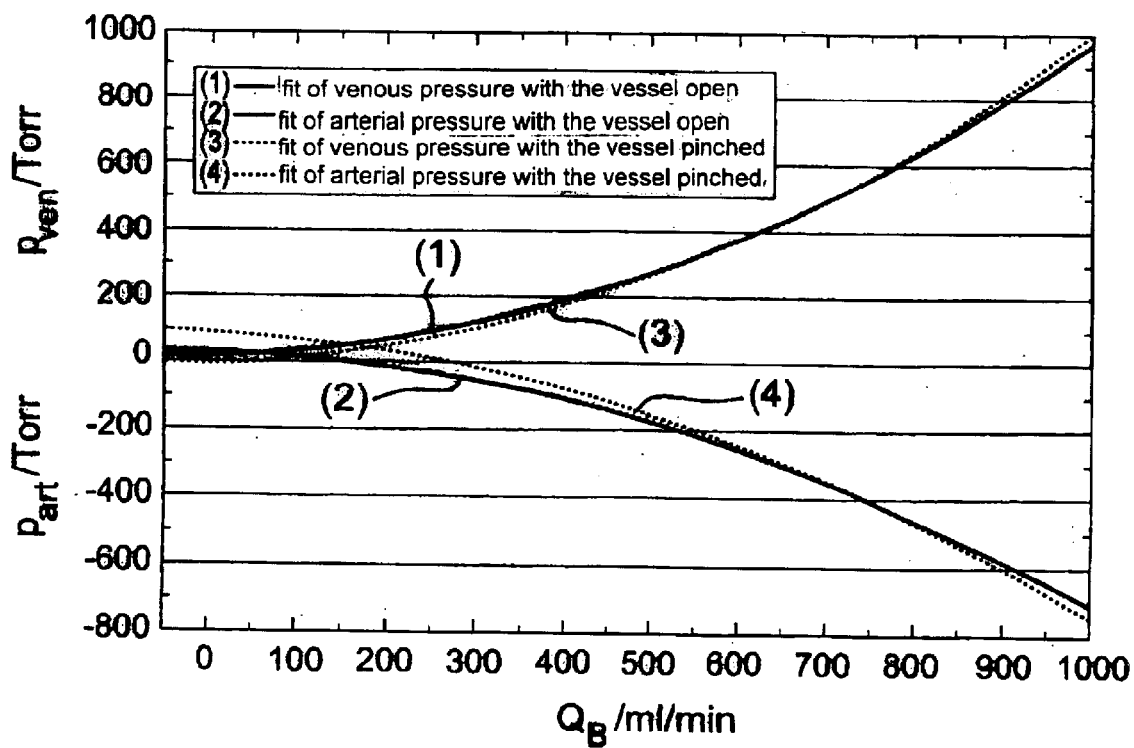
FIG. 3: shows a plot of the pressure in the arterial and/or venous branches of the extracorporeal circulation with the vascular access open and interrupted, as a function of the extracorporeal blood flow for a simultaneous dialysis treatment.

FIG. 3 shows the pressure-flow curve for a simulated dialysis treatment with the vascular access open and pinched at a fistula flow of 700±5 mL/min. The flow in the extracorporeal circulation is turbulent. Consequently, the function p=f($Q_B$) is nonlinear, but it can be approximated with quadratic polynomials of the type y=a+bx+cx$^2$ with a high correlation.

To measure the function $p=f(Q_B)$, the blood flow was varied in the range of between 50 to 550 mL/min, and the respective extracorporeal pressure was recorded. Then the functions were curve-fitted using the second degree polynomials and were extrapolated. The correlation coefficients were in the range of $R^2 > 0.998$.

With the blood pump stopped, the arterial pressure in the open vascular access is generally about 34 mm Hg, and the venous pressure is approximately 32 mm Hg. By compression of the vessel between the needles, the static arterial pressure is increased to approximately 94 mm Hg. This value thus corresponds to the average systemic pressure of the arterial system. The static venous pressure drops to approximately 7 mm Hg and reflects the return venous pressure. With an increase in blood flow, the initial pressure difference between the compressed vessel and the open vessel drops, because the pinched part of the vessel is bridged by the extracorporeal circulation to an increasing extent.

At the point of intersection of the respective arterial and venous function pairs $p=f(Q_B)$, it holds that Delta $p=0$. In the case when the extracorporeal pressure does not change with compression of the vessel, the resulting flow between the needles with the vessel open must consequently be zero, i.e., the fistula flow and the extracorporeal blood flow are identical. Thus, the fistula flow can be determined directly from the point of intersection of the respective $Q_B$ value.

The points of intersection of the second-degree polynomial functions are calculated by the following method. The second-degree polynomial for the pressure-flow curve with the vessel open can be written, for example, as follows:

$$y_1 = a_1 + b_1 x + c_1 x^2 \quad \text{(Equation 3)}$$

With the vessel pinched, the polynomial function can be written as:

$$y_2 = a_2 + b_2 x + c_2 x^2 \quad \text{(Equation 4)}$$

Equating equation 3 with equation 4 yields:

$$a_1 + b_1 x + c_1 x^2 = a_2 + b_2 x + c_2 x^2 \quad \text{(Equation 5)}$$

After converting:

$$(a_1 - a_2) + (b_1 - b_2)x + (c_1 - c_2)x^2 = 0 \quad \text{(Equation 6)}$$

With the following substitutions:

$(a_1 - a_2) = A$
$(b_1 - b_2) = B$
$(c_1 - c_2) = C$ the following two solutions are obtained for the mixed quadratic equation 6:

$$x_1 = \frac{-B + \sqrt{B^2 - 4AC}}{2C} \quad \text{(Equation 7)}$$

$$x_2 = \frac{-B - \sqrt{B^2 - 4AC}}{2C} \quad \text{(Equation 8)}$$

Equation 6 has two solutions which may either be different and real, identical and real or conjugated and complex. The selection of which case occurs is made according to the discriminant D:

$$D = B^2 - 4AC \quad \text{(Equation 9)}$$

If D is positive, there are two different real solutions. If $D=0$, there is a real double solution. However, if D is negative, equation 4 has two conjugated complex solutions. In the present case, D is always positive, so equation 4 supplies two different real points of intersection. Of these, only $x>0$ values are of physical interest, representing positive extracorporeal blood flow. Thus, the point of intersection in the pressure-flow curves being sought is defined by the positive solution of equations 7 and 8.

The following table summarizes the constants of the fitting computations of the type $y = a + bx + cx^2$ of the pressure-flow curve $p = f(Q_B)$ shown in FIG. 3.

| Pressure-flow curve | a | b | c | $R^2$ |
|---|---|---|---|---|
| Arterial with open vessel | 30.0714 | −0.07591 | $-6.66965 \cdot 10^{-4}$ | 0.99915 |
| Arterial with pinched vessel | 88.40084 | −0.13109 | $-7.050 \cdot 10^{-4}$ | 0.99970 |
| Venous with open vessel | 19.45073 | 0.08208 | $8.70911 \cdot 10^{-4}$ | 0.99988 |
| Venous with pinched vessel | −3.11153 | 0.0633 | $9.45423 \cdot 10^{-5}$ | 0.99994 |

Inserting the respective values into equation 6 and performing the calculation according to equations 7 and 8 yields the points of intersection derived from the following table:

| Value pair | Intersection Derived From eq. 7 | Intersection Derived From eq. 8 |
|---|---|---|
| Arterial pressure-flow curve | 723 mL/min | −2284 mL/min |
| Venous pressure-flow curve | −439 mL/min | 691 mL/min |

The fistula flow is calculated by averaging the appropriate solutions. In the range of positive flow, the average of the calculated flow in the vascular access is 707±23 mL/min.

Figure 4:
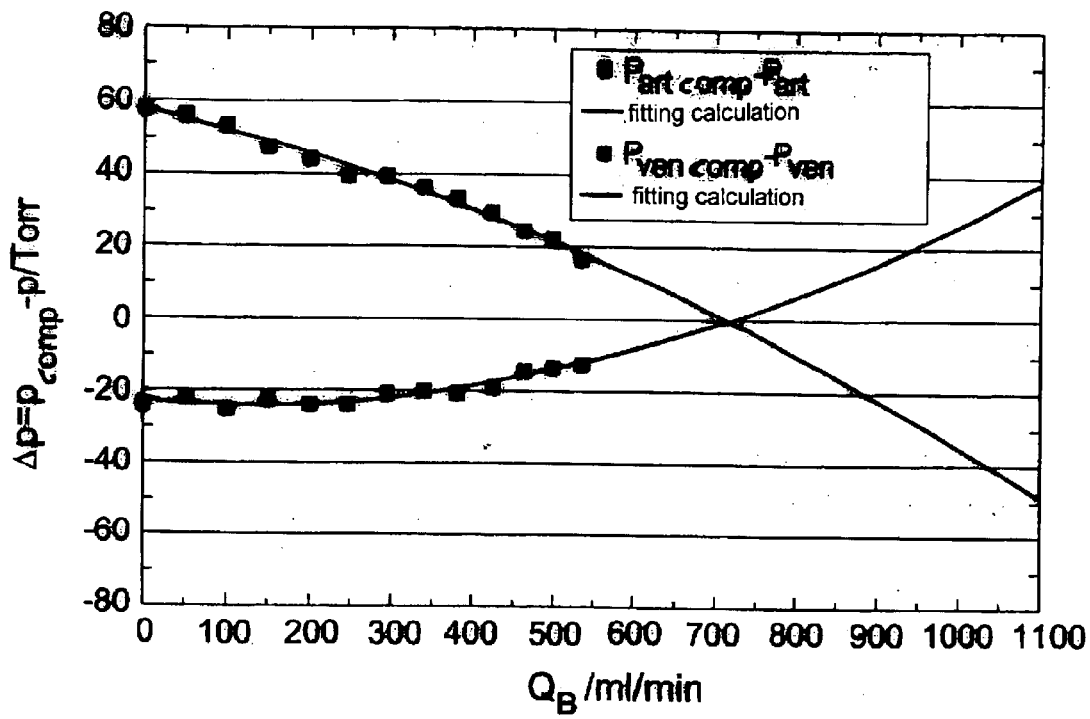
FIG. 4: shows a plot of the difference between the arterial or venous pressure with an interrupted vascular access and the arterial or venous pressure with an open vascular access, as a function of the extracorporeal blood flow for a simulated dialysis treatment.

FIG. 4 shows an alternative plot of the pressure measurement with the vascular access open and pinched. The pressure difference Delta p is plotted here as a function of the effective extracorporeal blood flow according to equations 1 and 2. The measured data were again fitted with second-degree polynomials. In the case when the extracorporeal pressure with the fistula open is the same as that with the fistula pinched (Delta $p=0$), extracorporeal blood flow and flow in the vascular access are identical. Consequently, the fistula flow can be determined from the common point of intersection of the polynomials, and also from the points of intersection of the individual polynomials with the x axis. The following table summarizes the constants of the curve-fitting calculation of the type $y = a + bx + cx^2$ from FIG. 4.

| Pressure difference | a | b | c | $R^2$ |
|---|---|---|---|---|
| Delta $p_{art} = (Q_B)$ acc. to eq. 1 | 58.24088 | −0.05247 | $-4.04643 \cdot 10^{-5}$ | 0.98834 |
| Delta $p_{ven} = (Q_B)$ acc. to eq. 2 | −22.90486 | −0.0149 | $-6.44045 \cdot 10^{-5}$ | 0.9222 |

Calculation of the point of intersection of the polynomials illustrated in FIG. 4 according to equations 7 and 8 yields a flow value of $Q_F = 719$ mL/min. The points of intersection of the polynomials with the x axis can be calculated by equating the y value to zero:

$$a + bx + cx^2 = 0 \quad \text{(Equation 10)}$$

By analogy with equation 6, the solution of the mixed quadratic equation 10 can thus be calculated from equations 7 and 8. The respective $Q_F$ values are 715 mL/min (from the arterial curve in FIG. 4) and 723 mL/min (from the venous curve in FIG. 4). In the method of fistula flow measurement, the arterial and venous pressures in the extracorporeal circulation can be recorded as a function of extracorporeal blood flow $Q_B$, while the dialysis treatment is underway.

The statistical determination of the static arterial and venous pressure can be carried out as follows. The function(s) $p_{art}$ $(Q_B)$ and $p_{ven}$ $(Q_B)$ are curve-fitted with quadratic polynomials of the type $y=a+bx+cx^2$. Then the y axis intercept a of the arterial and venous pressure-flow curves is calculated. The extracorporeal pressure is equal to the static pressure in the vascular access plus the hydrostatic pressure which comes about due to the differences in height between the extracorporeal pressure sensor and the vascular access. A pressure difference of approximately 0.77 mm Hg per cm of height difference can be assumed to be a good approximation.

Figure 5:
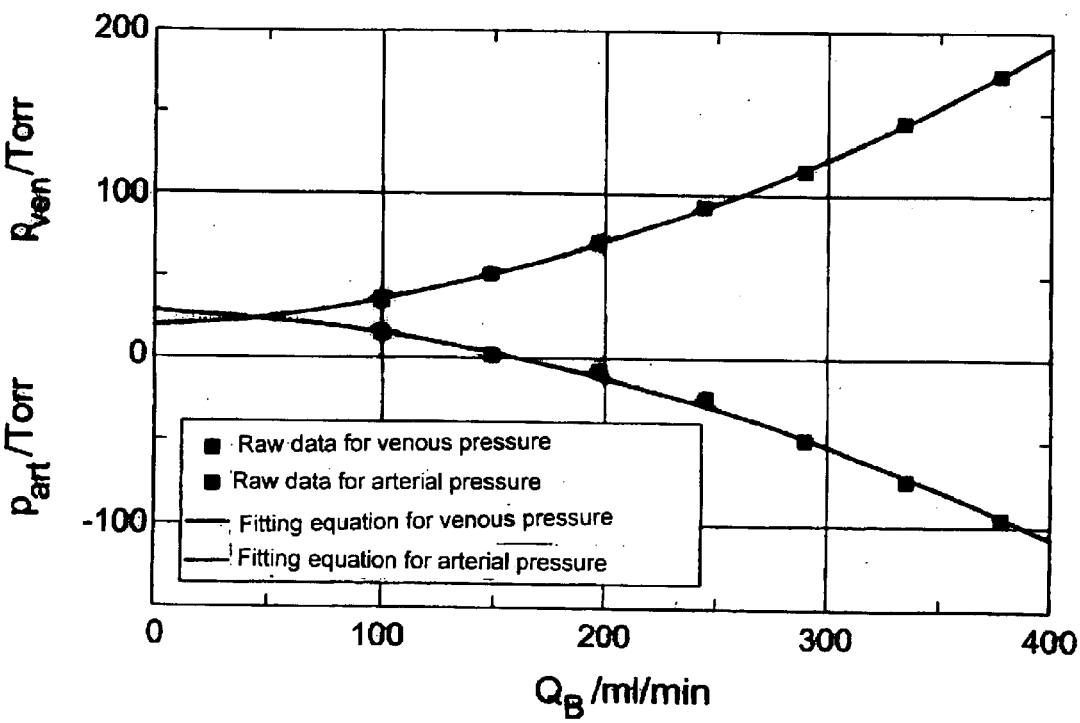
FIG. 5: shows a plot of the arterial or venous pressure as a function of the extracorporeal blood flow for a simulated dialysis treatment.

FIG. 5 shows the function value of the arterial and venous pressure-flow curve $p=f(Q_B)$ for a simulated dialysis treatment and the respective mathematical curve-fitting. Although the function $p=f(Q_B)$ is not linear, it can be curve-fitted with quadratic polynomials of the type $y=a+bx+cx^2$ with a high correlation. By using $x=0$ as a boundary condition, $y=a$ can be obtained, meaning that the point of intersection of the polynomial with the y axis can be defined by the polynomial constant a. The parameters shown in the following table can be obtained:

| Pressure-flow curve | a | b | c | $R^2$ |
| --- | --- | --- | --- | --- |
| Arterial extra-corporeal pressure | 30.0714 | −0.07591 | −6.66965 · $10^{-4}$ | 0.99915 |
| Venous extra-corporeal pressure | 19.45073 | 0.08208 | 8.709711 · $10^{-4}$ | 0.999888 |

The operation of the device for determining the fistula flow and the static arterial and venous pressure is described as follows. During the dialysis treatment, the control unit 18 initiates the measuring process, so that the blood flow $Q_B$ is increased continuously from a lower limit value within a predetermined range up to an upper value due to a change in the flow rate of the blood pump 16. As a result, venous pressure $P_{art}$, $P_{ven}$ is measured by the arterial or venous pressure measuring device 20,22. The measured values are stored in memory unit 25. Then the vascular access is pinched off between the arterial and venous needles. Control unit 18 then reduces the extracorporeal blood flow down to a lower limit value after starting from the upper limit value, for example, after confirmation being issued by the operating personnel, and then the arterial and venous pressure $P_{art\ comp}$ and $P_{ven\ comp}$ are measured again. The measured values can also be stored in memory unit 25. Computer unit 27 then can read out the stored measured values, and can calculate the fistula flow $Q_F$ and the static arterial and venous pressure in the fistula from the measured values, using one of the algorithms described above. The fistula flow and the fistula pressure can then be displayed on display unit 28.

What is claimed is:

1. A method of operating a blood treatment machine for determining a blood flow $Q_F$ in a vascular access of an extracorporeal circulation during an extracorporeal blood treatment, wherein blood entering a blood treatment unit of the blood treatment machine through an arterial connection of an arterial branch is in fluid connection with the vascular access, and is returned through a venous connection of a venous branch in fluid connection with the vascular access, the method comprising the steps of:

measuring at least one pair of pressures selected from the group consisting of $p_{art}$, $p_{art\ comp}$ and $p_{ven}$, $p_{ven\ comp}$, wherein $p_{art}$, $p_{art\ comp}$ are, respectively, the arterial branch pressure while the vascular access is open and blood flows through said vascular access between the arterial and venous connections, and while the vascular access is interrupted and no blood flows through the vascular access between the arterial and venous connections, while a blood flow $Q_B$ in the extracorporeal circulation is varied, and wherein $p_{ven}$, $p_{ven\ comp}$ are, respectively, the venous branch pressure while the vascular access is open and blood flows through said vascular access between the arterial and venous connections, and while the vascular access is interrupted and no blood flows through the vascular access between the arterial and venous connections, while the blood flow $Q_B$ in the extracorporeal circulation is varied; and calculating the blood flow $Q_F$ in the open vascular access between the arterial and venous connections from the measured values of the at least one pair of pressures selected from the group consisting of $p_{art}$, $p_{art\ comp}$ and $p_{ven}$, $p_{ven\ comp}$.

2. The method according to claim 1, further comprising the steps of:

varying the blood flow $Q_B$ in the extracorporeal circulation while the vascular access is open;

measuring at least one of the pressures $p_{art}$, $p_{ven}$ in the respective arterial and venous branches;

storing at least one of the pressures $p_{art}$, $p_{ven}$ measured with the vascular access open;

interrupting the vascular access between the arterial and venous connections;

varying the blood flow $Q_B$ in the extracorporeal circulation while the vascular access is closed;

measuring at least one of the pressures $p_{art\ comp}$, $p_{ven\ comp}$ in the respective arterial and venous branches; and storing at least one of the pressures $p_{art\ comp}$, $p_{ven\ comp}$ measured with the vascular access closed.

3. The method according to claim 1, further comprising the step of:

determining the blood flow in the open vascular access by measuring the blood flow $Q_B$ in the extracorporeal circulation in a condition when the pressure $p_{art\ comp}$ in the arterial branch with the vascular access interrupted is substantially equal to the pressure $p_{art}$ in the arterial branch with the vascular access open.

4. The method according to claim 1, further comprising the step of:

determining the blood flow in the open vascular access by measuring the blood flow $Q_B$ in the extracorporeal circulation at which the pressure $p_{ven\ comp}$ in the venous branch with the vascular access interrupted is substantially equal to the pressure $p_{ven}$ in the venous branch with the vascular access open.

5. The method according to claim 1, further comprising the step of:

measuring a first blood flow in the extracorporeal circulation at which the pressure $p_{art\ comp}$ in the arterial branch with the vascular access interrupted is substantially equal to the pressure $p_{art}$ in the arterial branch with the vascular access open;

measuring a second blood flow in the extracorporeal circulation at which the pressure $p_{ven\ comp}$ in the venous branch with the vascular access interrupted is equal to the pressure $p_{ven}$ in the venous branch with the vascular access open; and determining the blood flow in the open vascular access using the first and second flows.

6. The method according to claim 5, further comprising determining the blood flow in the open vascular access by averaging the first and second blood flow values.

7. The method according to claim 1, further comprising determining the blood flow in the open vascular access by measuring a value of the extracorporeal blood flow $Q_B$ at which a difference Delta $p_{art}$ between a pressure in the arterial branch with the vascular access interrupted and a pressure in the arterial branch with the vascular access open is equal to zero.

8. The method according to claim 1, further comprising determining the blood flow in the open vascular access by measuring a value of the extracorporeal blood flow $Q_B$ at which a difference Delta $p_{ven}$ between a pressure in the venous branch with the vascular access interrupted and a pressure in the venous branch with the vascular access open is equal to zero.

9. The method according to claim 1, further comprising the step of determining one of the arterial and venous static pressure in the vascular access by measuring a respective arterial and venous pressure $p_{art}$, $p_{ven}$ in the extracorporeal circulation at which blood flow in the extracorporeal circulation is equal to zero.

10. The method according to claim 1, further comprising;

measuring open values for the arterial and venous pressure in the respective arterial and venous branch of the extracorporeal circulation with the vascular access open;

measuring interrupted values for the arterial and venous pressure in the respective arterial and venous branch of the extracorporeal circulation with the vascular access interrupted; and determining parameters of a function $p(Q_B)$ representing arterial and venous pressure as a function of the extracorporeal blood flow $Q_B$ from the respective open and interrupted values.

* * * * *